US000001023H

United States Statutory Invention Registration [19]

[11] Reg. Number: H1023

Wiseman, Sr.

[43] Published: Mar. 3, 1992

[54] REMOVABLE LENS COVER FOR PROTECTIVE COVERALLS

[75] Inventor: Timothy R. Wiseman, Sr., Richmond, Va.

[73] Assignee: E. I. Du Pont de Nemours and Company, Wilmington, Del.

[21] Appl. No.: 421,413

[22] Filed: Oct. 13, 1989

[51] Int. Cl.[5] ..... A61F 9/02; A42B 1/08

[52] U.S. Cl. ..... 2/438; 2/9; 2/84; 2/206; 2/422; 2/424; 2/434

[58] Field of Search ..... 2/8, 9, 79, 84, 206, 2/227, 422, 424, 426, 427, 431, 434, 438

[56] References Cited

U.S. PATENT DOCUMENTS

| | | | |
|---|---|---|---|
| 2,592,805 | 4/1952 | Hutchinson | 2/8 |
| 3,946,442 | 3/1976 | Wallander | 2/9 |
| 4,076,373 | 2/1978 | Moretti | 2/434 |
| 4,138,746 | 2/1979 | Bergmann | 2/424 |
| 4,179,756 | 12/1979 | Lucas | 2/434 |
| 4,215,436 | 8/1980 | Ketterer | 2/422 |
| 4,272,851 | 6/1981 | Goldstein | 2/79 |
| 4,428,081 | 1/1984 | Smith | 2/438 |
| 4,455,687 | 6/1984 | Johansson | 2/424 |
| 4,455,689 | 6/1984 | Boyer | 2/434 |
| 4,528,701 | 7/1985 | Smith | 2/438 |
| 4,542,538 | 9/1985 | Moretti et al. | 2/438 |
| 4,716,601 | 1/1988 | McNeal | 2/434 |
| 4,748,697 | 6/1988 | Hodnett | 2/438 |

FOREIGN PATENT DOCUMENTS

| | | | |
|---|---|---|---|
| 2511243 | 9/1976 | Fed. Rep. of Germany | 2/438 |

*Primary Examiner*—Linda J. Wallace

[57] ABSTRACT

In protective coveralls with a head covering with a transparent permanent lens over the face area, a separate removable lens cover attached over the permanent lens which is adapted for very rapid removal in situations when the lens cover is clouded by a foreign material.

9 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

REMOVABLE LENS COVER FOR PROTECTIVE COVERALLS

BACKGROUND OF THE INVENTION

The present invention relates to garments for providing protection to the wearer in a hazardous environment and more particularly relates to a removable lens cover attached over a permanent lens of a head covering of the protective coveralls which is adapted for very rapid removal in situations when the lens cover is clouded by a foreign material.

Various types of protective coveralls are known for use in protecting the wearer of the coveralls from hazards including flame, hot and/or corrosive chemicals, molten metals, and the like. One such type of coveralls includes a one-piece suit for the body, arms and legs and a separate, removable head covering is worn together with the one-piece suit. The coveralls generally have a laminated construction with a durable, usually waterproof, outer shell which is impervious to the hazards to be encountered and a liner which increases the protection against high temperature conditions and may also include additional barrier layers.

The head covering of such suits typically includes an internal hard hat which supports a downwardly-draping hood of the outer shell material with liner about the wearer's head and may included a hood bib which extends downwardly about the chest and back of the wearer. So that the wearer can see, the hood has an opening at the face area which is covered by a transparent viewing lens. While suits with head covering of this type are capable of providing protection from the hazards to be encountered for specified limited periods, the wearer is at risk if his vision is obscured by the viewing lens becoming clouded by a foreign material, e.g., a leaking hot chemical sprayed onto the viewing lens. If the wearer cannot see well enough to escape quickly from the hazard, the exposure limits of the suit may be exceeded and injury may result. Even worse, the wearer may be forced to remove the head covering in order to see for his escape and be injured due to direct exposure.

SUMMARY OF THE INVENTION

The invention relates to improved protective coveralls having a main suit for covering the torso, arms and legs of wearer and a head covering with a transparent permanent viewing lens over the face of the wearer. In accordance with the invention, a separate removable transparent lens cover is provided which is dimensioned to cover at least a substantial portion of the viewing area of the exterior of the permanent lens. The lens cover is removably attached to the head covering with said lens cover overlying the exterior of said permanent lens. A handhold attached to the lens cover enables the wearer to grasp the handhold and very rapidly detach the removable lens in the event that the lens cover becomes clouded by a foreign material.

In accordance with a preferred form of the invention, the lens cover is attached to the head covering by attachment to the permanent lens with pressure-sensitive adhesive. In accordance with another preferred form of the invention, the handhold is provided by a pull tab, most preferably an extension of the lens cover, which extends from the lens cover past the periphery of the permanent lens.

BRIEF DESCRIPTION OF THE DRAWINGS

The invention and its advantages may be understood by reference to the following detailed description when read in conjunction with the accompanying drawings in which.

DETAILED DESCRIPTION

Figure 1:
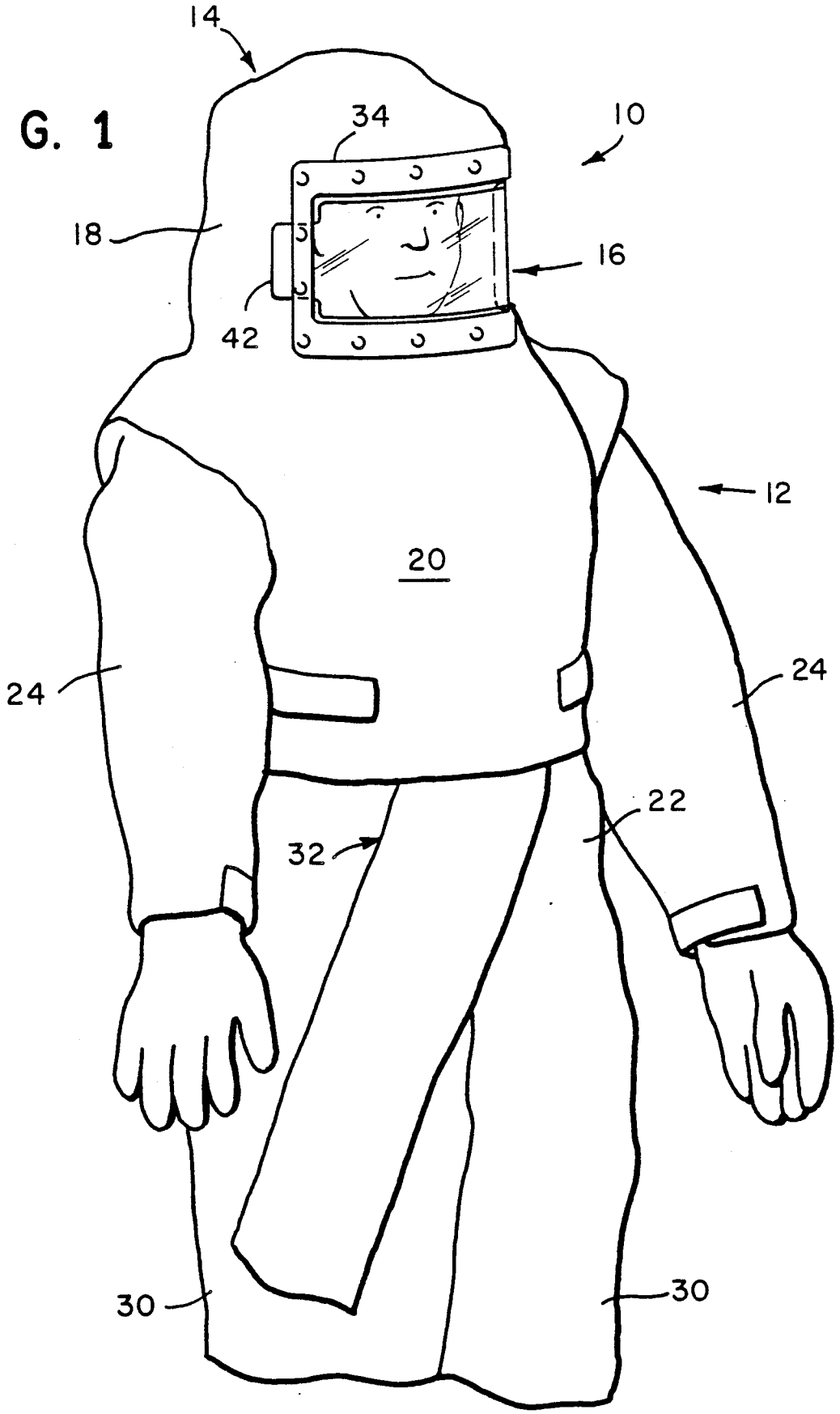
FIG. 1 is a somewhat diagrammatical perspective view of coveralls incorporating a preferred lens cover in accordance with the present invention.

Referring now to the drawings in which like reference characters designate like or corresponding parts throughout the several views, there is shown in FIG. 1 protective coveralls 10 embodying a preferred form of the present invention. The protective coveralls include a main suit 12 and a removable head covering 14. The head covering 14 includes a viewing lens 16 and a downwardly draping hood 18 for covering the head of the wearer of the coveralls 10 and which also includes a hood bib 20 covering the upper areas of the main suit 12 including the shoulders, chest and back of the wearer.

The coveralls 10 depicted are intended to represent coveralls which have any of a variety of laminated constructions for protection against hazards including steam, flame, and hot and/or corrosive chemicals which include a durable, usually liquid impervious outer shell and a thermal insulative inner liner which may include other barrier layers. The laminated construction is employed for most portions of the coveralls although the unlined shell may comprise portions of the suit which are not in direct contact with the body such as the hood bib 20. Suitable shell fabrics include woven aramid fabrics such as a fabric woven from poly(paraphenylene terephthalamide) which has been laminated to a liquid impervious layer such as an aluminum film-poly(ethylene terephthalate) film laminate. Suitable liner fabrics include multilayer laminates such as those employing at least a layer of woven poly(metaphenylene isophthalamide) and a nonwoven layer such as one or more layers of spun-laced fabric of poly(paraphenylene terephthalamide).

Referring still to FIG. 1, the main suit 12 includes a torso portion 22, sleeves 24 for covering the wearer's arms, and leg portions 30. A main closure 32 is provided in the main suit 12 for providing access into the suit.

Figure 2:
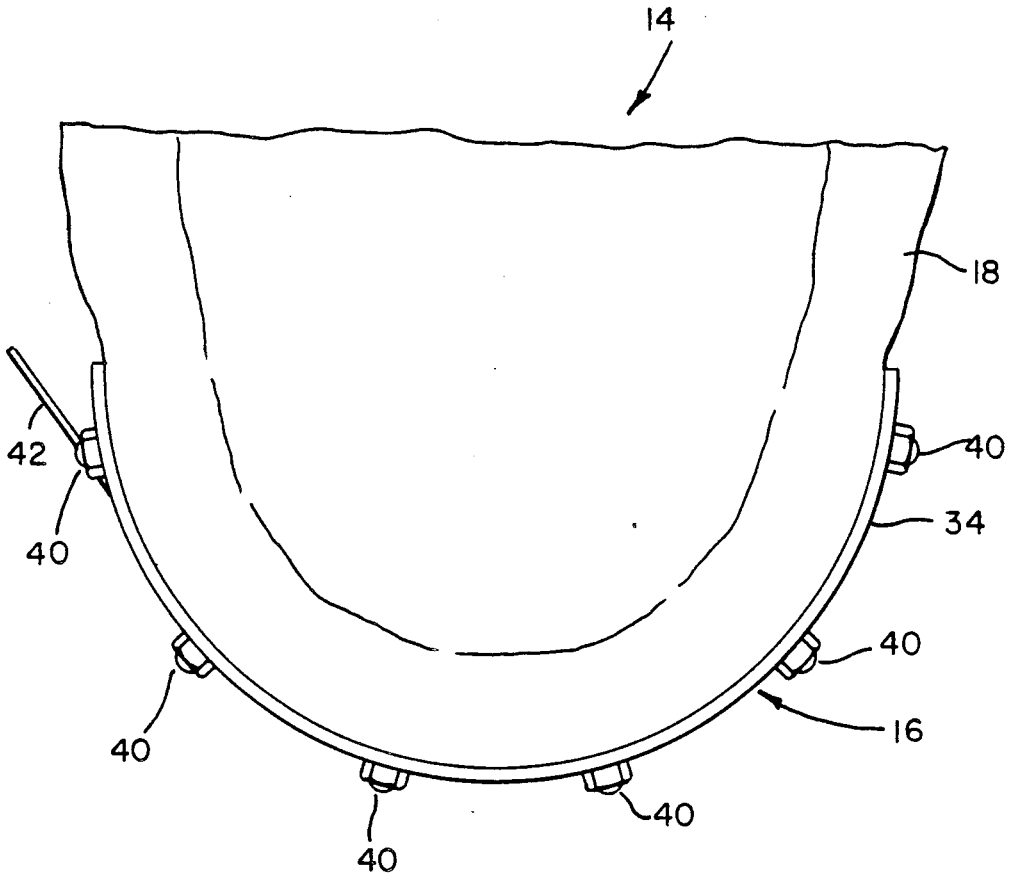
FIG. 2 is an enlarged partial plan view of head covering of the protective coveralls of FIG. 1.
Figure 4:
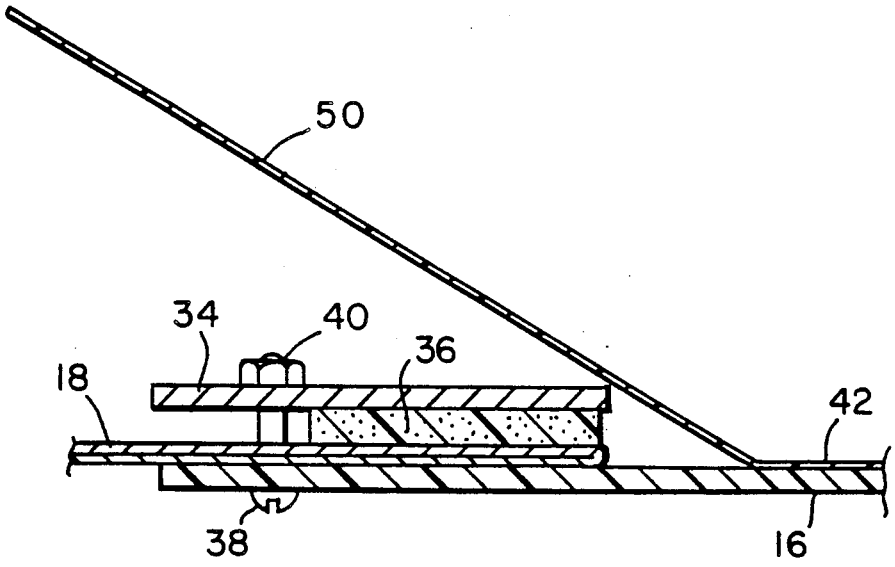
FIG. 4 is a partially diagrammatical cross-sectional view of a viewing lens mounting system for the coveralls of FIG. 1.

Referring now to FIGS. 1, 2 and 4, the viewing lens 16 of the head covering 14 is constructed using a metal frame 34 which frames an opening in the front of the hood 18 at a location corresponding to the face area of the wearer. The metal frame 34 which is shaped to conform to curvature of the hood 18 supports and is used to connect the permanent lens 16 to the hood 18. The permanent viewing lens 16 can be a shatter resistant transparent polymeric material which conforms to the shape of the frame 34. A preferred material for this purpose is the polycarbonate sheet having a thickness of 0.117 inches (3 mm) sold by General Electric under the trademark Lexan which has been heat set into a generally cylindrical configuration as is apparent from FIG. 2. Preferably, the cylindrical viewing lens 16 provides an arc of the cylinder at least about 165°, most preferably 180°, to give the wearer a field of view which is near normal in terms of width.

As shown in FIG. 4 which, for the purposes of illustration, does not show the curvature of the frame 34 and lens 16, a seal 36 such as a urethane foam seal corresponding to the dimensions of the frame is used between the frame 34 and the lens 16. The shell fabric of the hood 18, preferably hemmed to provided a double layer, is clamped between the seal and the lens 16. Bolts 38 and acorn nuts 40 provided in bores through the frame and lens or other suitable fasteners are used to pull the lens toward the frame to securely clamp the hood fabric.

Figure 3:
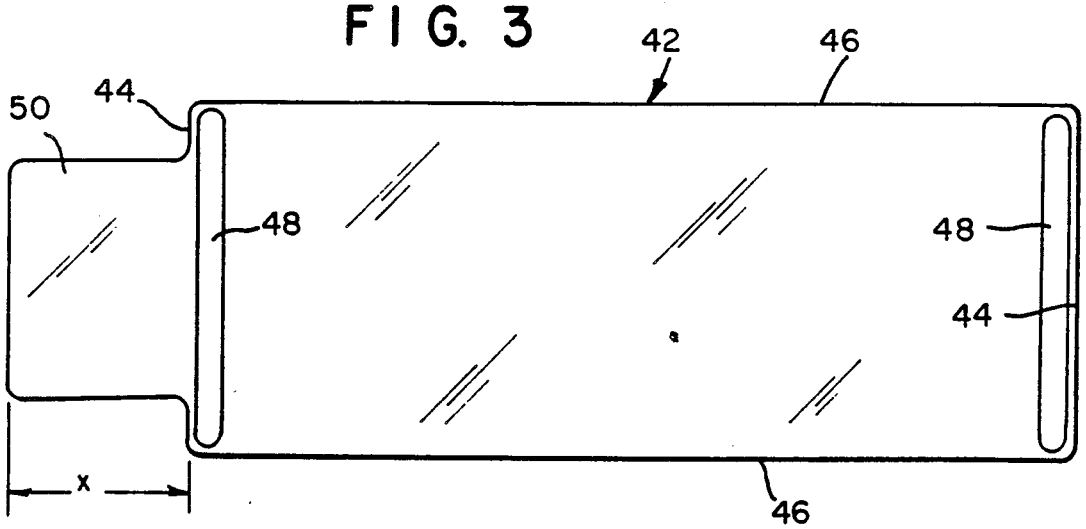
FIG. 3 is a plan view of the lens cover of the protective coveralls of FIG. 1 shown removed from the coveralls.

Referring now to FIGS. 1–4, the protective coveralls 10 include a removable lens cover 42. The lens cover 42 is attached to the head covering 10 but is adapted for quick removal by the wearer in the event that the lens cover 42 is clouded by a foreign material. The lens cover is preferably a thin, flexible polymeric sheet, most preferably provided by a poly(ethylene terephthalate) film having a thickness of between about 0.005 and about 0.01 inches (between about 0.13 mm and about 0.25 mm). The film is suitably dimensioned to cover a substantial portion, and most preferably substantially all of the exterior of the viewing lens 16. Preferably, an antistat is provided on the surface of the film to prevent it from collecting dust and other foreign materials. As shown in FIG. 3, it is preferable for the removable lens cover 42 to have a generally rectangular configuration which will overlie and correspond to the shape of the exterior surface of the viewing lens 16. As shown in FIG. 3, the removable lens cover 42 thus has two upright edges 44 and two horizontal edges 46.

In the preferred embodiment of the invention illustrated, the lens cover 42 is attached by means of pressure sensitive adhesive such as a clear acrylic adhesive. A suitable adhesive for this purpose is an adhesive identified as No. 444 sold by the 3M Corporation. In the preferred embodiment depicted, the adhesive is applied adjacent the upright edges 44 of the lens cover 42 so that the lens cover 42 is attached only along its upright edges 44 where at most only an insignificantly small degree of the peripheral vision of the wearer will be affected by the presence of the adhesive. Preferred locations for the adhesive on the lens cover 42 are identified by the character 48 in FIG. 3.

The removable lens cover 42 is provided with a handhold which facilitates removal by the wearer in the event that the lens cover 42 becomes clouded. In the embodiment depicted, the handhold is a pull tab which is an extension 50 of the lens cover 42 which extends outwardly from one of the upright edges 44 of the lens cover 42 by a distance "x" (FIG. 3) of between about 3 cm to about 8 cm. The extension 50 thus provides a pull tab for the removable lens 42 which extends outwardly past the periphery of the permanent lens 16. Because the permanent lens 16 is recessed within the frame 34 as shown in FIG. 4, the extension 50 is supported by the frame 34 in a position extending at an angle outwardly away from the frame 34 and the hood 18 and thus is in a position to be grasped easily.

In use, the removable lens cover 42 is used over the viewing lens 16 and the suit is used normally until there is a spill which causes the lens cover to be clouded and obscure the vision of the wearer. If this occurs, the wearer grasps the extension 50 of the removable lens cover 42 which forms the handhold and pulls outwardly and across to remove the lens cover 42 from the viewing lens 16. All covered portions of the viewing lens 16 will then be clear and the wearer of the coveralls will regain his vision and be able to escape from the hazard.

In FIG. 1, the lens cover 42 is attached so that the extension 50 which forms the pull tab is on the right side of the coveralls 10 from the perspective of the wearer. This configuration is well-suited for right-handed wearers who will naturally use their right hand to remove the lens cover 42. The lens cover 42 can be similarly attached with the extension 50 on the left side as desired by some left-handed wearers. At the option of the wearer, the extension can be positioned on the left side for a right-handed person, for example, and the wearer would reach across his face to grasp the pull tab and pull back toward the right to remove the lens cover 42.

The coveralls in accordance with the present invention decrease the risk of injury in the event that the wearer's vision is obscured due to chemical spills on the viewing lens. In addition, the removable lens cover provides protection for the viewing lens 16 in normal use. The polymeric sheet lenses typically used in suits of this type can be scratched and thus any scratches on the exterior of the lens which do occur will occur on the lens cover 42 and not the viewing lens 16. Thus, the lens cover 42 can be periodically replaced and thus prolong the life of the viewing lens 16.

While a preferred embodiment has been shown and described in the foregoing detailed description, it will be understood that the invention is capable of numerous modifications, rearrangements and substitution of parts without departing from the spirit of the invention as set forth in the appended claims.

I claim:

1. In protective coveralls for providing protection to a wearer of the coveralls in a hazardous environment, said coveralls having a main suit for covering the torso, arms and legs of the wearer and a head covering with a transparent permanent viewing lens over the face of the wearer, the improvement which comprises:

a separate removable transparent lens cover dimensioned to cover at least a substantial portion of the viewing area of the exterior of said permanent lens;

attachment means for removably attaching said lens cover to said head covering with said lens cover overlying the exterior of said permanent lens; and a pull tab attached to said removable lens and extending outwardly from the lens cover past the periphery of the permanent lens for providing a handhold for the wearer, whereby the wearer can grasp the pull tab and very rapidly detach the removable lens.

2. The protective coveralls of claim 1 wherein said removable lens is a thin, flexible polymeric sheet.

3. The protective coveralls of claim 2 wherein said thin, polymeric sheet is a sheet of poly(ethylene terephthalate).

4. The protective coveralls of claim 3 wherein said poly(ethylene terephthalate) sheet is between 0.13 mm and 0.25 mm thick.

5. The protective coveralls of claim 1 wherein said attachment means comprises pressure-sensitive adhesive for attaching said removable lens to said permanent lens.

6. The protective coveralls of claim 5 wherein said permanent lens is generally cylindrical in shape when viewed from above the head covering and said removable lens is rectangular in shape before attachment to the head covering and is flexible to conform to the shape of the generally cylindrical permenent lens following attachment to the head covering, said removable lens having two generally upright edges and two horizontal edges with said pressure-sensitive adhesive securing said removable lens adjacent said two generally upright edges.

7. The protective coveralls of claim 6 wherein said pull tab is attached adjacent to and extends outwardly from one of said upright edges of said removable lens.

8. The protective coveralls of claim 7 wherein said pull tab comprises an extension of said removable lens.

9. The protective coveralls of claim 8 wherein said extension of said lens extends outwardly from said upright edge of said lens cover by a distance of 3 cm and 8 cm.

* * * * *